(12) United States Patent
Yang et al.

(10) Patent No.: US 12,245,801 B2
(45) Date of Patent: Mar. 11, 2025

(54) ADJUSTABLE CRYOABLATION NEEDLE

(71) Applicant: ACCU TARGET MEDIPHARMA (SHANGHAI) CO., LTD., Shanghai (CN)

(72) Inventors: Chi Yang, Shanghai (CN); Binkai Xu, Shanghai (CN); Yinlong Wu, Shanghai (CN); Zhaohua Chang, Shanghai (CN)

(73) Assignee: ACCU TARGET MEDIPHARMA (SHANGHAI) CO., LTD., Shanghai (JP)

( * ) Notice: Subject to any disclaimer, the term of this patent is extended or adjusted under 35 U.S.C. 154(b) by 605 days.

(21) Appl. No.: 17/431,829

(22) PCT Filed: Jun. 17, 2020

(86) PCT No.: PCT/CN2020/096608
§ 371 (c)(1),
(2) Date: Aug. 18, 2021

(87) PCT Pub. No.: WO2021/027397
PCT Pub. Date: Feb. 18, 2021

(65) Prior Publication Data
US 2022/0160412 A1    May 26, 2022

(30) Foreign Application Priority Data
Aug. 13, 2019  (CN) .......................... 201910742034.0

(51) Int. Cl.
*A61B 18/02* (2006.01)
*A61B 17/00* (2006.01)
*A61B 18/00* (2006.01)

(52) U.S. Cl.
CPC .... *A61B 18/02* (2013.01); *A61B 2017/00424* (2013.01); *A61B 2017/00867* (2013.01);
(Continued)

(58) Field of Classification Search
CPC .......... A61B 18/02; A61B 2017/00424; A61B 2017/00867; A61B 2018/00101;
(Continued)

(56) References Cited

U.S. PATENT DOCUMENTS

| | | | |
|---|---|---|---|
| 2002/0087153 A1* | 7/2002 | Roschak | A61B 17/064 606/27 |
| 2017/0007310 A1* | 1/2017 | Rajagopalan | A61B 5/4255 |
| 2019/0059971 A1* | 2/2019 | Huang | A61L 31/026 |

FOREIGN PATENT DOCUMENTS

CN          203122580 U       8/2013

* cited by examiner

*Primary Examiner* — Ankit D Tejani
*Assistant Examiner* — Joshua Brendon Solomon
(74) *Attorney, Agent, or Firm* — NZ Carr Law Office

(57) ABSTRACT

Disclosed is an adjustable cryoablation needle, comprising a needle rod (3), a front-segment heat-insulated tube (1), a rear-segment heat-insulated tube (2), and an gas inlet structure (7) penetrating the needle rod (3) and the front-segment heat-insulated tube (1), wherein the needle rod (3) can move relative to the rear-segment heat-insulated tube (2) in the axial direction of the rear-segment heat-insulated tube (2) so as to adjust a first axial distance between the front end of the rear-segment heat-insulated tube (2) and the front end of the needle rod (3); and the front-segment heat-insulated tube (1) can move relative to the rear-segment heat-insulated tube (2) in the axial direction of the rear-segment heat-insulated tube (2). The adjustable cryoablation needle can prevent the inconvenience caused by a doctor selecting the model of the cryoablation needle.

20 Claims, 5 Drawing Sheets

(52) U.S. Cl.
CPC ............... *A61B 2018/00101* (2013.01); *A61B 2018/00577* (2013.01); *A61B 2018/0262* (2013.01); *A61B 2018/0293* (2013.01)

(58) Field of Classification Search
CPC .. A61B 2018/00577; A61B 2018/0262; A61B 2018/0293; A61B 2018/00184; A61B 2018/0237; A61B 2018/00047; A61B 90/08; A61B 90/04; A61B 2090/08021; A61B 2090/0463
See application file for complete search history.

ADJUSTABLE CRYOABLATION NEEDLE

TECHNICAL FIELD

The present disclosure relates to the field of medical appliances, and in particular to an adjustable cryoablation needle.

BACKGROUND

The existing cryoablation needles are often equipped with two types of needle rods, i.e., a short needle rod and a long needle rod. The length of the needle rod determines the depth of the needle tip inserted into the human body. If the location of a tumor is shallow and the needle insertion direction is safe and unobstructed, a cryoablation needle with a short needle rod can be selected and inserted in the tumor for cryoablation treatment. If the location of a tumor is deep (for example, when the patient is fat), or if the needle cannot be inserted from the shallower side and the needle needs to be inserted from the deeper side, a cryoablation needle with a long needle rod can be selected.

In a cryoablation surgery, when the needle rod is inserted into the human body, it is the safest if the needle rod is completely inserted into the human body. However, no matter whether a cryoablation needle with a long needle rod or a cryoablation needle with a short needle rod is selected, there is always a segment of the needle rod exposed out of the human body. When the exposed segment of the needle rod is relatively long, the needle rod will be bent due to the gravity of the cryoablation needle or other pulling forces. The bending may cause the leakage of the cold gas at a vacuum heat-insulated tube and also cause unnecessary pulling on human tissues, and in severe cases, it may tear the tissues and may break the needle rod. The longer exposed segment of the needle rod causes a greater torque relative to the human body and a higher risk factor.

It can be seen that in the related art, a cryoablation needle with a needle rod of a fixed length can hardly meet various treatment needs, and it is easy to cause an exposed portion of the needle rod during a surgery, thus causing the bending of the needle rod or causing an injury to the human body.

SUMMARY

The present disclosure provides an adjustable cryoablation needle to solve the problem that a cryoablation needle with a needle rod of a fixed length can hardly meet various treatment needs, and it is easy to cause an exposed portion of the needle rod during a surgery, thus causing the bending of the needle rod or causing an injury to the human body.

According to a first aspect of the present disclosure, providing an adjustable cryoablation needle, comprising: a needle rod, a front-segment heat-insulated tube and an gas inlet structure penetrating the needle rod and the front-segment heat-insulated tube, wherein the front-segment heat-insulated tube is inserted into the needle rod from a rear end of the needle rod, the front-segment heat-insulated tube can move relative to the needle rod in the axial direction of the needle rod. The gas inlet structure comprises a first gas inlet tube and a spring-like second gas inlet tube. The front end of the first gas inlet tube extends to the needle rod, and the rear end of the first gas inlet tube is connected to the front end of the second gas inlet tube. The adjustable cryoablation needle also comprises the rear-segment heat-insulated tube, and the front-segment heat-insulated tube is inserted into the rear-segment heat-insulated tube from a front end of the rear-segment heat-insulated tube; the needle rod can move relative to the rear-segment heat-insulated tube in the axial direction of the rear-segment heat-insulated tube so as to adjust a first axial distance between the front end of the rear-segment heat-insulated tube and the front end of the needle rod; the front-segment heat-insulated tube can move relative to the rear-segment heat-insulated tube in the axial direction of the rear-segment heat-insulated tube so as to adjust a second axial distance between the front end of the front-segment heat-insulated tube and the front end of the rear-segment heat-insulated tube; Wherein, the length of the effective needle rod segment of the adjustable cryoablation needle changes with the first axial distance; when the length of the effective needle rod segment changes, the front-segment heat-insulated tube can move relative to the needle rod in the axial direction of the needle rod so that the length of a targeting region of the adjustable cryoablation needle can change with the difference between the first axial distance and the second axial distance. the position of the first gas inlet tube is fixed relative to the needle rod, the rear end of the second gas inlet tube is directly or indirectly connected to a gas inlet passage, the position of the gas inlet passage is fixed relative to the rear-segment heat-insulated tube, and the second gas inlet tube can be compressed or stretched along the axial direction.

Optionally, the adjustable cryoablation needle further comprises a needle rod adjusting structure for driving the needle rod to move relative to the rear-segment heat-insulated tube in the axial direction of the rear-segment heat-insulated tube, and the needle rod adjusting structure is fixedly connected to the outer side of the needle rod.

Optionally, the adjustable cryoablation needle further comprises a handle; the needle rod is inserted into the handle from the front end of the handle, and the rear-segment heat-insulated tube is arranged in the handle and is fixed in position relative to the handle; the length of the effective needle rod segment is an axial distance between the front end of the handle and the front end of the needle rod; a tube wall of the handle is provided with a needle rod adjusting groove along the axial direction, and the needle rod adjusting structure passes through the needle rod adjusting groove and can move along the needle rod adjusting groove.

Optionally, the adjustable cryoablation needle further comprises a targeting region adjusting structure for driving the front-segment heat-insulated tube to move relative to the rear-segment heat-insulated tube in the axial direction, the targeting region adjusting structure is fixedly connected to the outer side of the front-segment heat-insulated tube.

Optionally, the needle rod adjusting structure is provided with a targeting region adjusting groove in the axial direction, and the targeting region adjusting structure passes through the targeting region adjusting groove and can move along the targeting region adjusting groove.

Optionally, the targeting region adjusting structure comprises a targeting region slider fixedly connected to the front-segment heat-insulated tube and a targeting region lever connected to the targeting region slider, and the targeting region lever is located outside the needle rod adjusting groove and/or the targeting region adjusting groove.

Optionally, the needle rod adjusting structure comprises a needle rod slider fixedly connected to the needle rod and a needle rod lever connected to the needle rod slider, and the needle rod lever is located outside the needle rod adjusting groove.

Optionally, the targeting region adjusting groove is configured in the needle rod lever, and the targeting region lever is located in the needle rod adjusting groove and/or the targeting region adjusting groove.

Optionally, the gas inlet structure further comprises a finned tube and a mandrel, the finned tube is wound around the mandrel, the front end of the finned tube is connected to the rear end of the second gas inlet tube, the rear end of the finned tube is directly or indirectly connected to the gas inlet passage, and the position of the mandrel is fixed relative to the rear-segment heat-insulated tube.

Optionally, when the effective needle rod segment reaches the minimum length, the second gas inlet tube is in a natural state without being stretched.

Optionally, the material of the second gas inlet tube is any one of stainless steel, spring steel and memory metal material.

Optionally, the gas inlet structure further comprises a mandrel, the second gas inlet tube is wound around the mandrel, and the position of the mandrel relative to the rear-segment heat-insulated tube is fixed.

Optionally, heat exchanging fins are configured on the surface of the second gas inlet tube.

Optionally, the adjustable cryoablation needle further comprises a needle rod sealing assembly located at the rear end of the needle rod, and the needle rod sealing assembly is used to seal a gap between the inner wall of the needle rod and the outer wall of the front-segment heat-insulated tube.

Optionally, the adjustable cryoablation needle further comprises a rear heat-insulated tube sealing assembly located at the front end of the rear-segment heat-insulated tube; the rear heat-insulated tube sealing assembly is used to seal a gap at the inner side of the inner wall of the rear-segment heat-insulated tube.

Optionally, the front-segment heat-insulated tube comprises a front-segment inner tube and a front-segment outer tube, a front-segment vacuum interlayer is formed between the front-segment inner tube and the front-segment outer tube, the front end of the front-segment inner tube is connected to the front end of the front-segment outer tube, and the rear end of the front-segment inner tube is connected with the rear end of the front-segment outer tube.

Optionally, the rear end of the front-segment inner tube and the rear end of the front-segment outer tube are connected by a heat-insulated tube gasket, and the rear end of the heat-insulated tube gasket has a tapered inner hole.

Optionally, the front-segment heat-insulated tube has a first tube segment, a connecting tube segment, and a second tube segment in the axial direction, respectively; the rear end of the first tube segment is connected to the front end of the connecting tube segment, the rear end of the connecting tube segment is connected to the front end of the second tube segment, the inner diameter of the second tube segment is greater than the inner diameter of the first tube segment, and the outer diameter of the second tube segment is greater than the outer diameter of the first tube segment.

Optionally, the rear-segment heat-insulated tube comprises a rear-segment inner tube and a rear-segment outer tube, a rear-segment vacuum interlayer is formed between the rear-segment inner tube and the rear-segment outer tube, the front end of the rear-segment inner tube is connected with the front end of the rear-segment outer tube, and the rear end of the rear-segment inner tube is connected with the rear end of the rear-segment outer tube.

In the adjustable cryoablation needle provided by the present disclosure, the first axial distance between the front end of the rear-segment heat-insulated tube and the front end of the needle rod is adjustable, and the length of the effective needle rod segment of the adjustable cryoablation needle changes with the first axial distance, thereby, the length of the effective needle rod segment in the adjustable cryoablation needle that can be used for needle insertion is changeable; and thus the present disclosure can freely change the length according to different treatment requirements, in order to satisfy various treatment requirements. Therefore, the present disclosure can avoid the inconvenience caused by the fact that a doctor has to select the type of cryoablation needles, and can be well adapted to different needle insertion depths, so that the exposed needle rod part can be as short as possible, and the bending of the needle rod and an injury to human tissues such as tissue tearing can be avoided.

Moreover, the length of the targeting region (or effective freezing area) of the cryoablation needle is related to the freezing range. For example, if the targeting region becomes longer, an ice ball formed by freezing will be larger. In some technologies, the length of the targeting region of the cryoablation needle is usually fixed, so that doctors need to select cryoablation needles with different targeting region lengths according to the tumor size. It can be seen that even if the length of the effective needle rod is indeed changeable, if the length of the targeting region remains the same, it is difficult to meet the treatment requirements of tumors of different sizes with one cryoablation needle. Doctors still need to select cryoablation needles with different targeting region lengths according to the tumor size.

Furthermore, in the present disclosure, the length of the targeting region may also change as the length of the effective needle rod segment changes; thus, the length of the targeting region is controllable and no longer changes synchronously with the change of the effective needle rod segment; the length of the targeting region is not fixed either, and its change may have a certain degree of freedom and is not completely limited to the movement of the needle rod. Therefore, the present disclosure can use a cryoablation needle to meet different needle depths and at the same time to further meet the treatment requirements of tumors of different sizes, and there is no need to select different cryoablation needles for different tumor sizes.

In addition, in the present disclosure, adjustment is achieved, and the position of the needle rod can be fixed relative to the first gas inlet tube of the J-T groove. To avoid the distance between the front end of the first gas inlet tube and the needle tip is too large by fixing the position of the needle rod relative to the first gas inlet tube. Therefore, it can prevent the problem that an ice ball cannot completely cover the needle tip, thus preventing the risk of puncturing the organs and blood vessels. Meanwhile, it can also prevent the needle rod from being ejected by a high-pressure gas, further improving the safety.

BRIEF DESCRIPTION OF THE DRAWINGS

To describe examples of the present disclosure or technical solutions in the existing art more clearly, the drawings required in description of the embodiments or the existing art will be briefly described below. Apparently, the drawings referred to in the following description are merely some embodiments of the present disclosure, and those skilled in the art may also conclude other drawings based on these drawings without contributing creative efforts.

DESCRIPTION OF REFERENCE NUMERALS

1—Front-segment heat-insulated tube;
101—Front-segment outer tube;
102—Front-segment inner tube;
103—Heat-insulated tube gasket;
104—First tube segment;
105—Second tube segment;
106—Connecting tube segment;
2—Rear-segment heat-insulated tube;
201—Rare-segment outer tube;
202—Rare-segment inner tube;
3—Needle rod;
301—Needle tip;
4—Effective needle rod segment;
5—Targeting region;
6—Heat-insulating area;
7—Gas inlet structure;
701—First gas inlet tube;
702—Second gas inlet tube;
703—Gas inlet passage;
704—Finned tube;
705—Mandrel;
706—Throttle hole;
8—Gas return structure;
9—Rear heat-insulated tube sealing assembly;
901—Rear heat-insulated tube sealing gasket;
902—Rear heat-insulated tube front retainer gasket;
903—Rear heat-insulated tube rear retainer gasket;
10—Targeting region adjusting structure;
1001—Targeting region slider;
1002—Targeting region lever;
11—Handle;
1101—Needle rod adjusting groove;
12—Needle rod sealing assembly;
1201—Needle rod sealing gasket;
1202—Needle rod front retainer gasket;
1203—Needle rod rear retainer gasket;
13—Needle rod adjusting structure;
1301—Needle rod slider;
1302—Needle rod lever;
1303—Targeting region adjusting groove;
1304—Front limiting portion
1305—Rear limiting portion.

DETAILED DESCRIPTION

Technical solutions in the examples of the present disclosure will be clearly and completely described below in conjunction with the drawings in the examples of the present disclosure. Apparently, the examples described are merely some examples rather than all examples of the present disclosure. Based on the examples of the present disclosure, all other examples obtained by those skilled in the art without any creative efforts would fall within the protection scope of the present disclosure.

In the description, the claims and the drawings of the present disclosure, the terms "first", "second", "third", "fourth", etc. (if existing) are used for distinguishing similar objects rather than describing a specific order or sequence. It should be understood that the data used in this way may be interchanged under appropriate circumstances so that the examples of the present disclosure described herein may be implemented in an order other than those illustrated or described herein. In addition, the terms "including" and "comprising" and any variations thereof are intended to cover non-exclusive inclusions. For example, a process, method, system, product, or device that includes a series of steps or units is not necessarily limited to those clearly listed steps or unit, but may also include other steps or unit that are not clearly listed or are inherent to the process, method, product, or device.

The technical solutions of the present disclosure will be described in detail below with specific examples. The following specific examples may be combined with each other, and the same or similar concepts or processes may not be repeated in some examples.

Figure 1A:
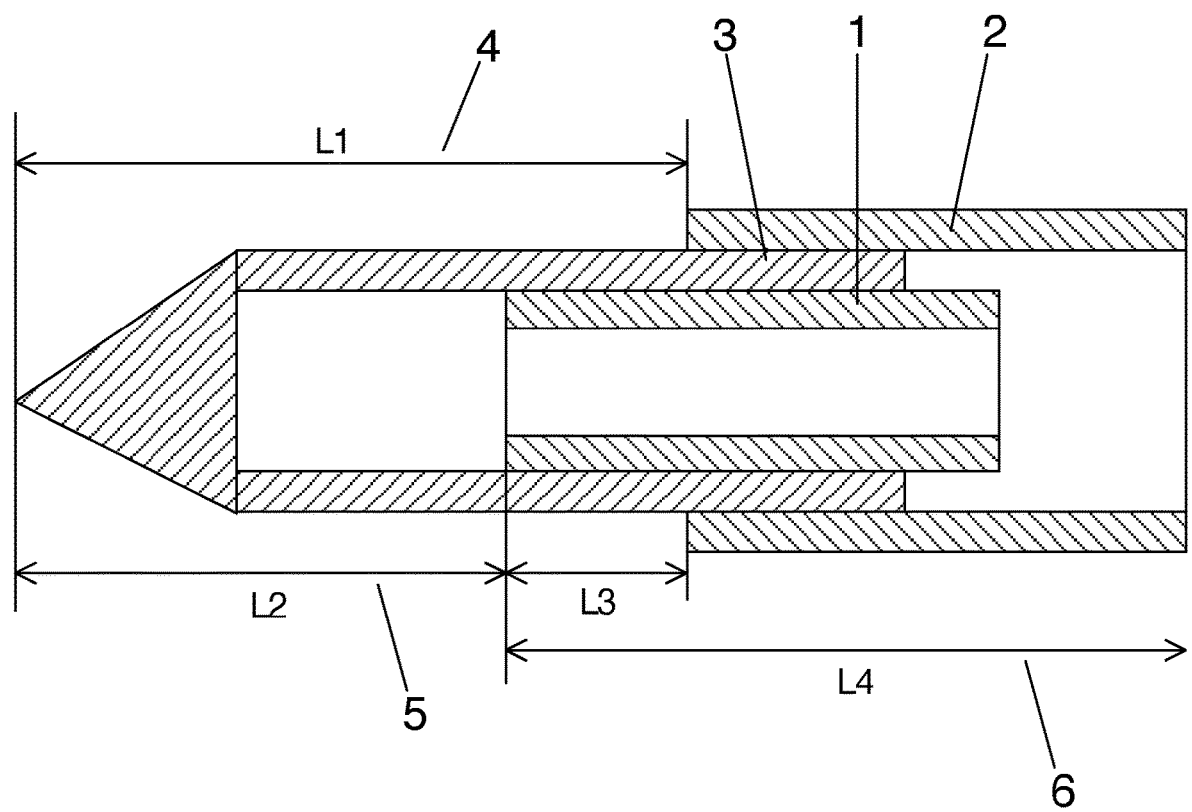
FIG. 1a is schematic diagram 1 of the principle of an adjustable cryoablation needle in an embodiment of the present disclosure.
Figure 1B:
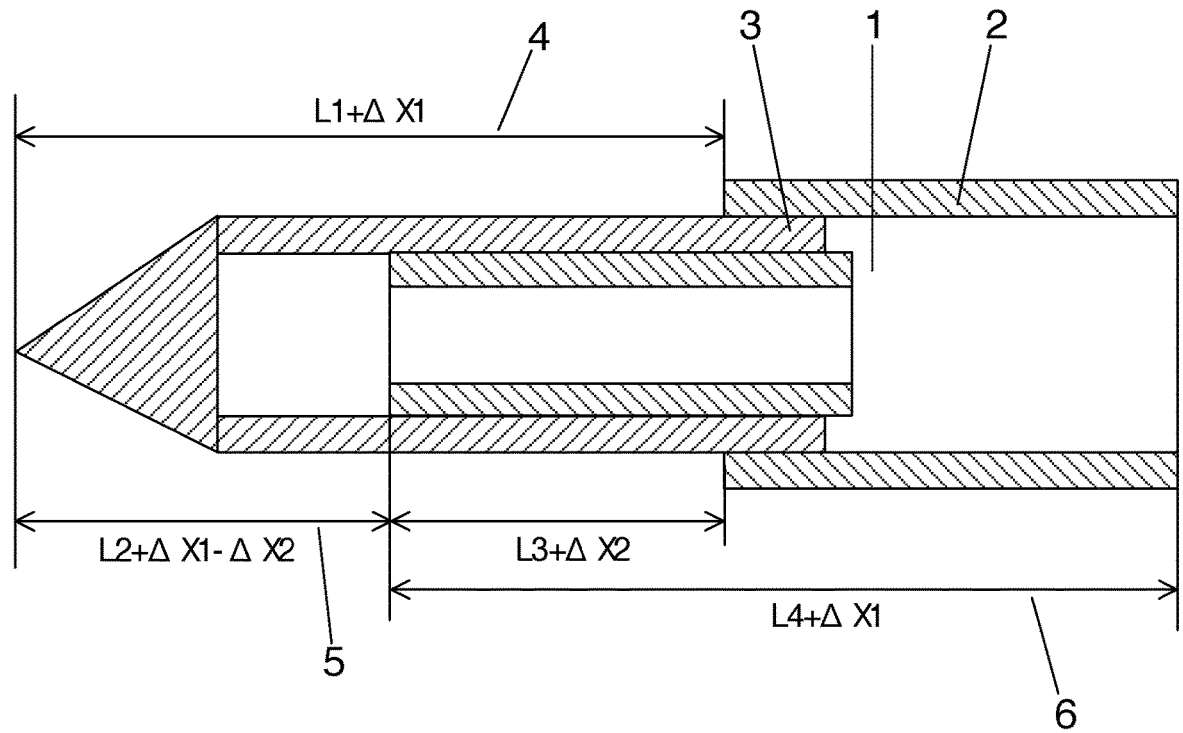
FIG. 1b is schematic diagram 2 of the principle of an adjustable cryoablation needle in an embodiment of the present disclosure.
Figure 2:
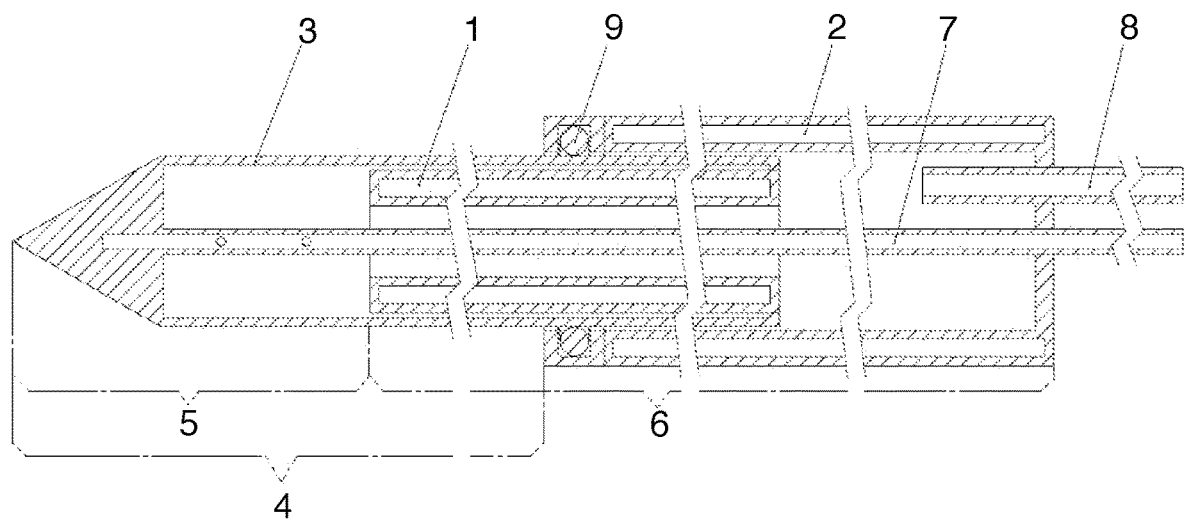
FIG. 2 is schematic diagram 3 of the principle of an adjustable cryoablation needle in an embodiment of the present disclosure.

FIG. 1*a* is schematic diagram 1 of the principle of an adjustable cryoablation needle in an embodiment of the present disclosure; FIG. 1*b* is schematic diagram 2 of the principle of an adjustable cryoablation needle in an embodiment of the present disclosure; FIG. 2 is schematic diagram 3 of the principle of an adjustable cryoablation needle in an embodiment of the present disclosure.

Referring to FIG. 1*a* and FIG. 1*b*, the adjustable cryoablation needle comprises: a needle rod 3, a front-segment heat-insulated tube 1, and a rear-segment heat-insulated tube 2; the front-segment heat-insulated tube 1 is inserted into the needle rod 3 from the rear end of the needle rod 3, and the front-segment heat-insulated tube 1 is also connected to the rear-segment heat-insulated tube 2 from the front end of the rear-segment heat-insulated tube 2. After assembling, the needle rod 3, the front-segment heat-insulated tube 1 and the rear-segment heat-insulated tube 2 share the same axial direction.

From the above description, the position and assembly relationship among the front-segment heat-insulated tube 1, the rear-segment heat-insulated tube 2 and the needle rod 3 can be seen, and based on this relationship, any shape change and any structure addition will not depart from the description of this embodiment.

In this embodiment, the needle rod 3 can move relative to the rear-segment heat-insulated tube 2 in the axial direction of the rear-segment heat-insulated tube 2, so as to adjust a first axial distance between the front end of the rear-segment heat-insulated tube 2 and the front end of the needle rod 3, and the length of the first axial distance can be represented by L1 and L1+ΔX1 as shown in FIG. 1a and FIG. 1b.

The length of the effective needle rod segment 4 of the adjustable cryoablation needle may change with the first axial distance;

Wherein, in this embodiment, it can achieve a variable-length heat-insulating area through the front-segment heat-insulated tube and rear-segment heat-insulated tube. In the heat-insulating area, the back end of the heat-insulating area can be guaranteed to always be in the desired position, which makes sure that the heat-insulating area can always cover the position where the heat insulation is required, and it is not difficult to maintain coverage due to the movement of the heat-insulated tube. For example, at least part of the gas inlet structure (further, for example, the second gas inlet tube) may be kept in the heat-insulating area at all times. That is to say, only in the need to change the length of the heat-insulating area, so as to give consideration to the coverage of the heat-insulating and the length of the targeting region, the front-segment heat-insulated tube and rear-segment heat-insulated tube need to be generated.

Wherein, the length of the effective needle rod segment 4 here can be understood as the length of the exposed tube segment of the needle rod 3 for needle insertion, that is, the insertable segment of the surgery.

In one example, it may be equal to the first axial distance. Meanwhile, FIG. 1a, FIG. 1b and FIG. 3 all use the first axial distance to represent the effective needle rod segment 4. In another example, a side at the front end of the rear-segment heat-insulated tube 2 of the adjustable cryoablation needle may be equipped with some structural parts for protection, limit or other functions, they can surround the outside of the needle rod 3, and the exposed part of the needle rod will be relatively reduced, and thus the length of the effective needle rod segment 4 can be less than the first axial distance. No matter which solution is adopted, the length of the effective needle rod segment 4 can change with the first axial distance.

It can be seen that, in the above implementation, the first axial distance between the front end of the rear-segment heat-insulated tube and the front end of the needle rod is adjustable, and the length of the effective needle rod segment of the adjustable cryoablation needle changes with the first axial distance, so the length of the effective needle rod segment in the adjustable cryoablation needle that can be used for needle insertion is changeable, and thus the length can be changed freely in the above implementation according to different treatment requirements, thereby satisfying various treatment requirements. Therefore, the above implementation can avoid the inconvenience caused by the fact that a doctor has to select the type of cryoablation needles, and can be well adapted to different needle insertion depths, so that the exposed needle rod part can be as short as possible, and the bending of the needle rod and an injury to human tissues such as tissue tearing can be avoided.

However, when the effective needle rod segment 4 changes, if the heat-insulated tubes are unchanged, a longer effective needle rod segment corresponds to a longer targeting region, and accordingly a bigger ice ball is formed, and in this case, at a deep position in the human body, only large tumors can be ablated; a shorter effective needle rod segment corresponds to a shorter targeting region, and accordingly a smaller ice ball is formed, and in this case, at a shallow position in the human body, only small tumors can be ablated. Therefore, when the length of the targeting region changes with the adjustment of the length of the effective needle rod segment, the treatment requirements for tumors of different depths and sizes cannot be satisfied.

When the effective needle rod segment 4 changes and the effective needle rod segment becomes longer, if the front heat-insulated tube and the needle rod are kept moving together so that the targeting region remains unchanged, the size of the ice ball formed will not change, which hardly satisfies the treatment requirements for tumors of different sizes.

Therefore, in this embodiment, through the implementation shown in FIG. 1a and FIG. 1b, the free change of the length of the targeting region can be achieved, which is beneficial to avoiding the problem that the targeting region can only be lengthened synchronously or remain unchanged when the effective needle rod segment becomes longer.

Wherein, the front-segment heat-insulated tube 1 can move relative to the rear-segment heat-insulated tube 2 in the axis of the rear-segment heat-insulated tube, so as to adjust the second axial distance between the front end of the front-segment heat-insulated tube 1 and the front end of the rear-segment heat-insulated tube 2, wherein the length of the second axial distance can be represented as L3 and L3+ΔX2 shown in FIG. 1a and FIG. 1b.

Referring to FIG. 1a and FIG. 1b, when the length of the effective needle rod segment 4 changes, the front-segment heat-insulated tube 1 can move relative to the needle rod 3 in the axial direction of the needle rod 3 so that the length of the targeting region of the adjustable cryoablation needle can change with the difference between the first axial distance and the second axial distance.

Taking FIG. 1a and FIG. 1b as examples, when the needle rod 3 moves in the axial direction, its first axial distance can be extended from L1 to L1+ΔX1. The front-segment heat-insulated tube 1 can also extend forward, and the length of the front-segment heat-insulated tube 1 extending out of the rear-segment heat-insulated tube 2 can be changed from L3 to L3+ΔX2. Correspondingly, the length of the targeting region 5 can be changed from L2 to L2+ΔX1−ΔX2, and the length of the heat-insulating area 6 can be changed from L4 to L4+ΔX2.

The length of the targeting region (or effective freezing area) of the cryoablation needle is related to the freezing range. For example, if the targeting region becomes longer, an ice ball formed by freezing will be larger. In some technologies, the length of the targeting region of the cryoablation needle is usually fixed, so that doctors need to choose cryoablation needles with different targeting region lengths according to the tumor size. It can be seen that even if the length of the effective needle rod is indeed changeable, if the length of the targeting region remains the same, it is difficult to meet the treatment requirements of tumors of different sizes with one cryoablation needle. Doctors still need to choose cryoablation needles with different targeting region lengths according to the tumor size.

Furthermore, in the above implementation, the length of the targeting region may also change as the length of the effective needle rod segment changes; thus, the length of the targeting region is controllable and no longer changes synchronously with the change of the effective needle rod segment; the length of the targeting region is not fixed either, and its change may have a certain degree of freedom and is not completely limited to the movement of the needle rod. Therefore, the present disclosure can use a cryoablation needle to meet different needle depths and at the same time to further meet the treatment requirements of tumors of different sizes, and there is no need to select different cryoablation needles for different tumor sizes.

Meanwhile, in this embodiment, on the one hand, through the relative movement of the two heat-insulated tubes, it is not difficult to maintain the coverage of part of the required positions in the heat-insulating area due to the movement of the heat-insulated tube. On the other hand, it can also be conducive to the achievement of the regulation of the targeting region mentioned above, so as to give consideration to the coverage of the heat-insulated area and the regulation of the targeting region.

Referring to FIG. 2, since the front-segment heat-insulated tube 1 is inserted into the rear-segment heat-insulated tube 2 from the front end of the rear-segment heat-insulated tube 2, there can always be an overlapping area between the front-segment heat-insulated tube 1 and the rear-segment heat-insulated tube 2, thus preventing cold gas inside the needle from leaking out.

Please referring to FIG. 2, each heat-insulated tube here can be specifically understood as a tube structure in which a vacuum gap layer can be formed. The structure form in which the vacuum gap layer is formed can be arbitrary, and its specific examples can be given in the relevant description below.

Wherein, in one embodiment, the adjustable cryoablation needle may further comprise a gas inlet structure 7 and/or a gas return structure 8. The gas inlet structure 7 can be inserted into/penetrating the needle rod 3 and the front-segment heat-insulated tube 1.

Wherein, the front end of the gas inlet structure 7 can be extended to the needle rod 3; specifically, the front end of the gas inlet structure 7 can extend to a position close to the front end of the needle rod 3, for example, it can extend to the needle tip of the needle rod 3. The rear end of the gas inlet structure 7 can be connected to the outside via a gas inlet passage, for example, it can be directly or indirectly connected to a gas source.

The front end of the gas return structure 8 can extend to the side of the rear end of the needle rod 3 and the front-segment heat-insulated tube 1, and may be located at the inner side of the rear-segment heat-insulated tube 2. The gas return structure 8 can be understood as any structure that can guide the gas flowing through the needle rod 3 to return back. The rear end of the gas return structure 8 can be directly or indirectly connected to a device such as vacuum equipment to provide power for the return of gas.

Figure 3:
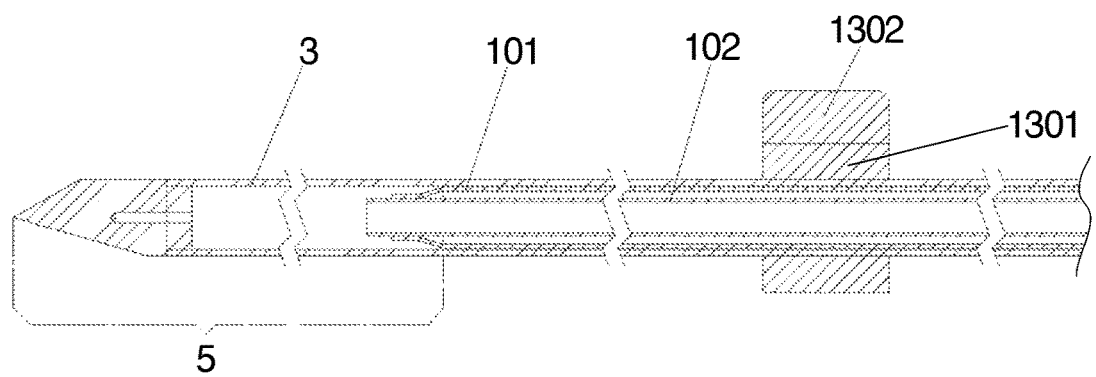
FIG. 3 is a partial cross-sectional view of the needle rod, the needle rod adjusting structure and the front-segment heat-insulated tube in an embodiment of the present disclosure.
Figure 4:
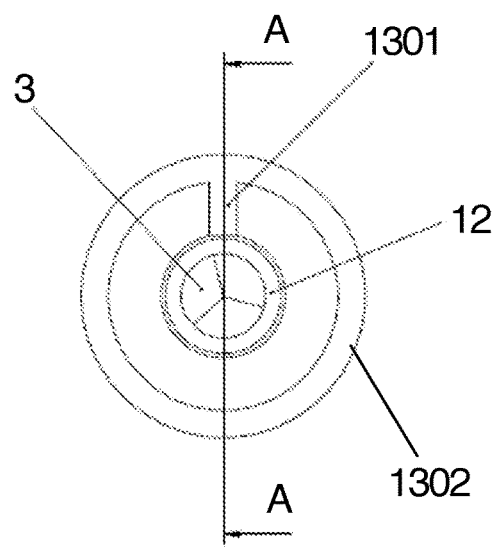
FIG. 4 is a schematic diagram of the end faces of the needle rod and the needle rod adjusting structure in an embodiment of the present disclosure.
Figure 5:
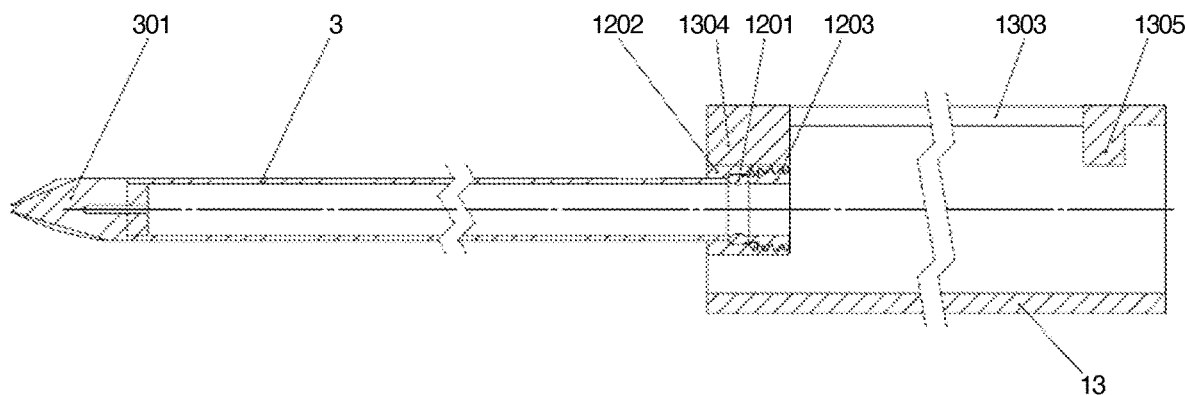
FIG. 5 is a schematic diagram of section A-A in FIG. 4.
Figure 6:
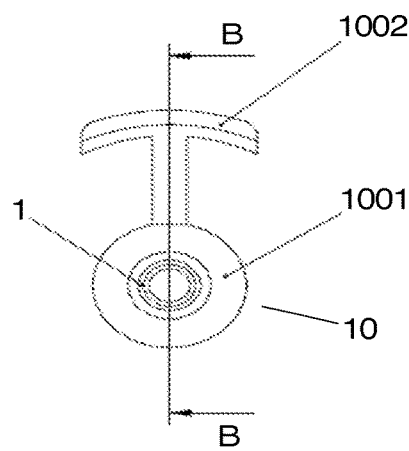
FIG. 6 is a schematic diagram of the end faces of the front-segment heat-insulated tube and the targeting region adjusting structure in an embodiment of the present disclosure.
Figure 7:
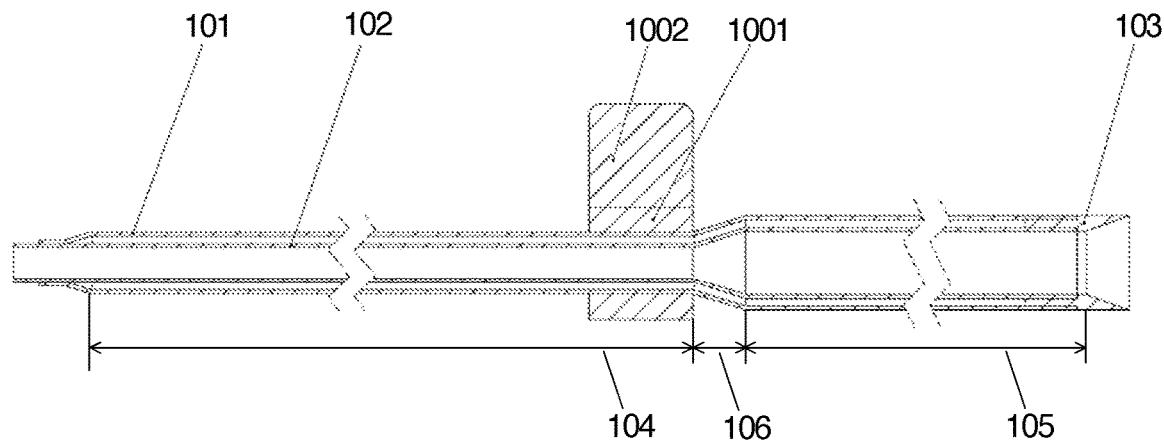
FIG. 7 is a schematic diagram of section B-B in FIG. 6.
Figure 8:
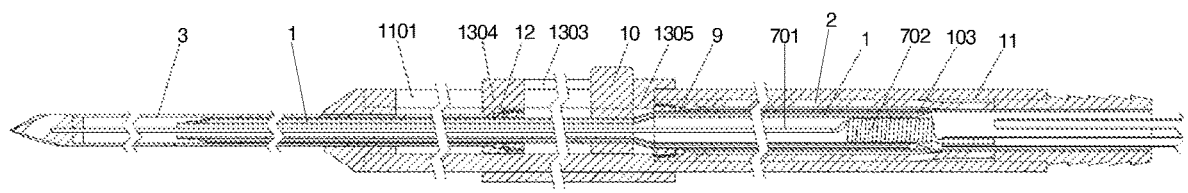
FIG. 8 is schematic diagram of an adjustment position of an adjustable cryoablation needle in an embodiment of the present disclosure.
Figure 9:
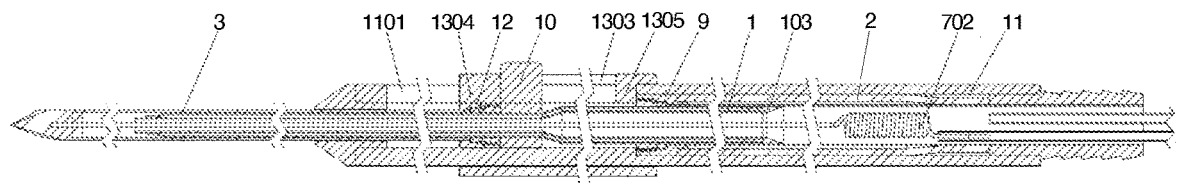
FIG. 9 is schematic diagram of another adjustment position of an adjustable cryoablation needle in an embodiment of the present disclosure.
Figure 10:
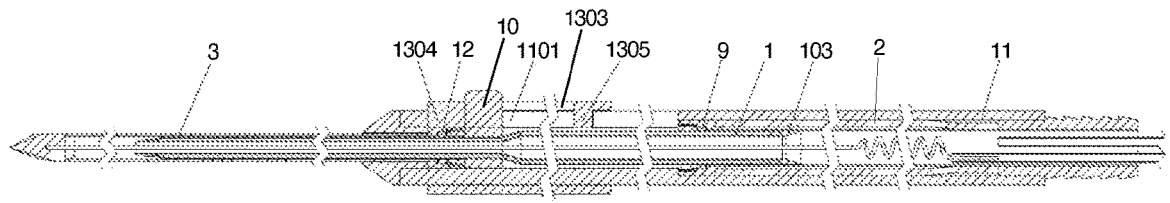
FIG. 10 is schematic diagram of yet another adjustment position of an adjustable cryoablation needle in an embodiment of the present disclosure.

FIG. 3 is a partial cross-sectional view of the needle rod, the needle rod adjusting structure and the front-segment heat-insulated tube in one embodiment of the present disclosure. FIG. 4 is a schematic diagram of the end faces of the needle rod and the needle rod adjusting structure in one embodiment of the present disclosure; FIG. 5 is a schematic diagram of section A-A in FIG. 4; FIG. 6 is a schematic diagram of the end faces of the front-segment heat-insulated tube and the targeting region adjusting structure in an embodiment of the present disclosure; FIG. 7 is a schematic diagram of section B-B in FIG. 6; FIG. 8 is schematic diagram of an adjustment position of an adjustable cryoablation needle in an embodiment of the present disclosure; FIG. 9 is schematic diagram of another adjustment position of an adjustable cryoablation needle in an embodiment of the present disclosure; FIG. 10 is schematic diagram of yet another adjustment position of an adjustable cryoablation needle in an embodiment of the present disclosure;

Referring to FIGS. 3 to 10, the adjustable cryoablation needle further comprises a needle rod adjusting structure 13 for driving the needle rod 3 to move relative to the rear-segment heat-insulated tube 2 in the axial direction, and the needle rod adjusting structure 13 is fixedly connected to the outer side of the needle rod 3.

Referring to FIGS. 8 to 10, the adjustable cryoablation needle further comprises a handle 11. The handle 11 here can also be understood as a knife shell.

The needle rod 3 is inserted into the handle 11 from the front end of the handle, and the rear-segment heat-insulated tube 2 is arranged in the handle 11 and is fixed in position relative to the handle 11. Based on the arrangement of the handle 11, the length of the effective needle rod segment may be the axial distance between the front end of the handle 11 and the front end of the needle rod 3.

Referring to FIGS. 8 to 10, the tube wall of the handle 11 is provided with a needle rod adjusting groove 1101 in the axial direction, and the needle rod adjusting structure 13 passes through the needle rod adjusting groove 1101 and can move along the needle rod adjusting groove 1101.

Taking FIGS. 8 and 9 as examples, the needle rod 3 with the rear-segment heat-insulated tube 2 can move relative to the handle 11 backwards to an extreme position. At this time, it can be restricted by the rear end of the needle rod adjusting groove 1101. Taking FIG. 10 as an example again, the needle rod 3 with the rear-segment heat-insulated tube 2 can move forward to the extreme position relative to the handle 11, and at this time, it can be restricted by the front end of the needle rod adjusting groove 1101.

Since the needle rod adjusting structure 13 is fixedly connected to the needle rod 3, the movement of the needle rod adjusting structure 13 in the axial direction is the movement of the needle rod 3 in the axial direction. By moving the needle rod adjusting structure 13, the needle rod 3 can move in the axial direction. It can be seen that the needle rod adjusting structure 13 can provide an operable structure for the movement operation of the needle rod 3 located inside, so as to facilitate the manipulation and movement of the needle rod 3.

Referring to FIG. 4 and FIG. 5, in the specific implementation process, the needle rod adjusting structure 13 may comprise a needle rod slider 1301 and a needle rod lever 1302 connected to the needle rod slider 1301, the needle rod lever 1302 is located outside the needle rod adjusting groove 1101. Correspondingly, the needle rod slider 1301 can be clamped in the needle rod adjusting groove 1101, and then move along the needle rod adjusting groove 1101.

In the implementation shown in FIGS. 6 to 10, in order to achieve the adjustment of the targeting region, the adjustable cryoablation needle may further comprise a targeting region adjusting structure 10 for driving the front-segment heat-insulated tube 1 to move relative to the rear-segment heat-insulated tube 2 in the axial direction. The targeting region adjusting structure 10 is fixedly connected to the outer side of the front-segment heat-insulated tube 1, and thus the targeting region adjusting structure 10 can provide an operable structure for the movement operation of the front-segment heat-insulated tube 1 of the needle rod located inside, thereby facilitating the manipulation and movement of the front-segment heat-insulated tube 1.

In a specific implementation process, the targeting region adjusting structure 10 can be independent of the needle rod adjusting structure 13. In order to facilitate the manipulation of the targeting region adjusting structure 10, corresponding adjusting grooves can be formed in the front-segment heat-insulated tube 1 and/or the handle 11 so that the targeting region adjusting structure 10 can pass through the adjusting grooves and move along the adjusting grooves. For example, the targeting region adjusting groove mentioned below can also be formed in the handle 11, and then the targeting region adjusting groove and the needle rod adjusting groove may be misaligned in the axial direction.

In another specific implementation process, the needle rod adjusting structure 13 can also be combined with the targeting region adjusting structure 10, as shown in FIG. 4 to FIG. 10.

Referring to FIG. 4 and FIG. 10, the needle rod adjusting structure 13 is provided with a targeting region adjusting groove 1303 in the axial direction, and the targeting region adjusting structure 10 passes through the targeting region adjusting groove 1303 and can move along the targeting region adjusting groove 1303. Correspondingly, a front limiting portion 1304 and a rear limiting portion 1305 for limiting the targeting region adjusting structure 10 are respectively formed at the front and back ends of the targeting region adjusting groove 1303.

Referring to FIG. 4, the cross-section of the needle rod lever 1302 of the needle rod adjusting structure 13 may be a ring-shaped structure. Furthermore, the needle rod adjusting structure 13 may be tubular. It can be seen that the needle rod adjusting structure 13 can be divided into a needle rod lever 1302 and a needle rod slider 1301 in the radial direction, and can be divided into a front limiting portion 1304 and a rear limiting portion 1305 in the axial direction.

The width of the needle rod slider 1301 in the circumferential direction may be less than the width of the needle rod adjusting groove 1101. Correspondingly, the width of the needle rod lever 1302 in the circumferential direction may be greater than the width of the needle rod adjusting groove 1101, so that the needle rod lever 1302 can always be located outside the needle rod adjusting groove 1101, which is convenient for manipulation.

Referring to FIG. 8, in this case, the position of the needle rod adjusting structure 13 may be at the rear end of the needle rod adjusting groove 1101, and the position of the targeting region adjusting structure 10 may be at the rear end of the targeting region adjusting groove 1303.

Referring to FIG. 9, as compared with FIG. 8, it can be understood that when the position of the needle rod adjusting structure 13 is unchanged, the position of the targeting region adjusting structure 10 can be at the front end of the targeting region adjusting groove 1303 by moving forward. Correspondingly, the front-segment heat-insulated tube 1 can move forward to the corresponding position, so that the length of the targeting region can be minimized when the length of the effective needle rod segment remains unchanged.

Referring to FIG. 10, as compared with FIG. 9, it can be understood that the position of the needle rod adjusting structure 13 can be at the foremost end of the needle rod adjusting groove 1101 by moving forward, and meanwhile, since the targeting region adjusting structure 10 is in the targeting region adjusting groove 1303, the needle rod adjusting structure 13 can be driven to move together by pushing the targeting region adjusting structure 10; and by virtue of the synchronous movement of the targeting region adjusting structure 10 and the needle rod adjusting structure 13, the position of the targeting region adjusting structure 10 is always at the front end of the targeting region adjusting groove 1303, and the needle rod adjusting structure 13 moves to the front end of the needle rod adjusting groove 1101. Correspondingly, both the front-segment heat-insulated tube 1 and the needle rod 3 can extend forward to the foremost end, so as to maximize the length of the effective needle rod segment; at the same time, since the positions of the front-segment heat-insulated tube 1 and the needle rod 3 always remain unchanged, the length of the targeting region will not change.

It can be seen that by shifting the needle rod adjusting structure 13 back and forth, the needle rod 3 can be driven to move back and forth, so as to adjust the length of the effective needle rod segment, and by shifting the targeting region adjusting structure 10 back and forth, the entire front-segment heat-insulated tube 1 can be driven to move back and forth, so as to adjust the length of the targeting region.

Meanwhile, the length of the targeting region can only be adjustable within a certain range, due to the limitation of the targeting region adjusting groove 1303, thus preventing the targeting region from being too long and causing frostbite to normal human tissues.

In the specific implementation process, referring to FIG. 6 and FIG. 7, the targeting region adjusting structure 10 may comprise a targeting region slider 1001 fixedly connected to the front-segment heat-insulated tube 1 and a targeting region lever 1002 connected to the targeting region slider 1001, and the targeting region lever 1002 can be located outside the targeting region adjusting groove 1303 and/or the needle rod adjusting groove 1101.

The targeting region slider 1001 can be understood as a structure for connecting the targeting region lever located outside the targeting region adjusting groove 1303 and the front-segment heat-insulated tube 1, and the width of this structure in the circumferential direction may be less than the targeting region adjusting groove 1303; correspondingly, the circumferential width of the targeting region lever 1002 can be greater than the width of the targeting region adjusting groove 1303, so that the targeting region lever 1002 can always be located outside the targeting region adjusting groove 1303, which is convenient for manipulation.

In addition, in the targeting region adjusting groove 1303 and the needle rod adjusting groove 1101, a safe locking groove for locking and positioning the corresponding lever or slider can also be provided. Through the safety locking grooves, it is convenient to lock the relative position between the targeting region adjusting structure 10 and the targeting region adjusting groove 1303 and the relative position between the needle rod adjusting structure 13 and the needle rod adjusting groove 1101. Wherein, if the friction force between the needle rod and the heat-insulated tubes is large enough, the position locking may not be performed through the safe locking grooves mentioned above, and only the friction force may be used. It can be seen that no matter whether the safe locking grooves are provided, it does not depart from the description of this embodiment.

Figure 11:
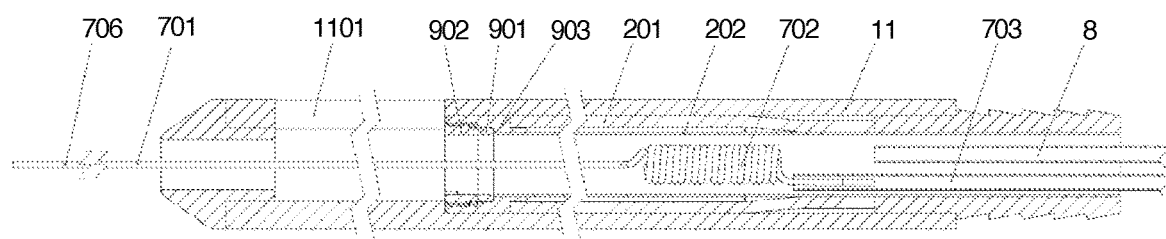
FIG. 11 is partial cross-sectional view 1 of an adjustable cryoablation needle in an embodiment of the present disclosure.
Figure 12:
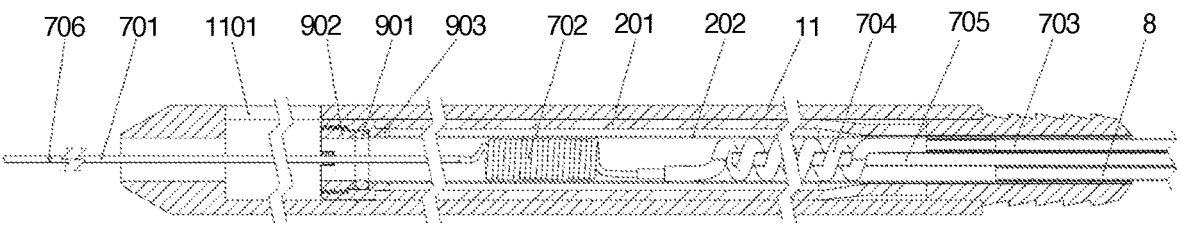
FIG. 12 is partial cross-sectional view 2 of an adjustable cryoablation needle in an embodiment of the present disclosure.

FIG. 11 is partial cross-sectional view 1 of an adjustable cryoablation needle in one embodiment of the present disclosure; and FIG. 12 is partial cross-sectional view 2 of an adjustable cryoablation needle in one embodiment of the present disclosure.

Referring to FIG. 11 and FIG. 12 in conjunction with other drawings, the gas inlet structure 7 comprises a first gas inlet tube 701 and a spring-like second gas inlet tube 702. The first gas inlet tube 701 may adopt a J-T groove. The J-T groove can be, for example, inserted into the needle rod 3 until it reaches the needle tip 301, and the J-T groove is also inserted into a counterbore at the rear end of the needle tip 301 to be welded and fixed.

In comparison, in some existing art, for the purpose of adjusting the targeting region, the relative position between the needle rod 3 and the gas inlet tube such as the J-T groove is not fixed to each other. In this case, because the gaps among the knife shell, the needle rod and the J-T groove are too large, the formed ice ball is located at the rear side of the needle tip, and the ice ball cannot completely cover the needle tip, so that a knife head will hurt other tissues. It can be seen that it will cause the ice ball to fail to cover the needle tip, thus increasing the risk of surgical puncture.

Specifically, if the needle rod and the J-T groove are not fixed to each other, during the adjustment of the targeting region, for example, since the position of the J-T groove is usually fixed relative to the heat-insulated tubes, the J-T groove and the freezing medium sprayed from the J-T groove cannot form a flow state in the needle rod space in front of the J-T groove, which will cause the ice ball to fail to cover the needle tip completely. If the ice ball cannot cover the needle tip, this results in that the needle tip completely passes through a tumor and is insert into normal tissues during the surgery. If the tumor is close to large blood vessels or important organs, there is a great risk of puncture if the needle tip completely penetrates the tumor.

In addition, by fixing the needle rod to the J-T groove, the needle rod can be further prevented from being ejected by high-pressure gas, which adds a safety guarantee and makes the surgery safer.

The front end of the first gas inlet tube 701 extends to the needle rod 3, specifically to the needle tip 301 of the needle rod 3. The position of the first gas inlet tube 701 relative to the needle rod 3 is fixed, and the rear end of the first gas inlet tube 701 is connected to the front end of the second gas inlet tube 702, the rear end of the second gas inlet tube 702 is directly or indirectly connected to the gas inlet passage 703, and the position of the gas inlet passage 703 is fixed relative to the rear-segment heat-insulated tube 2.

The second gas inlet tube 702 can be understood as a spring-like structure that can be stretched and compressed in the axial direction. The movement requirements of the needle rod 3 relative to the rear-segment heat-insulated tube 2 and the handle 11 can be met through the stretching and contraction of the spring-like structure.

In addition, the spring-like second gas inlet tube can be understood as a hollow tube, for example, it can be an independent spring, or it can be formed by winding a J-T groove. It can be seen that the first gas inlet tube and the second gas inlet tube can be made of the same material or different materials. Wherein the material of the second gas inlet tube may specifically be a memory metal material, or it may be stainless steel, spring steel, or Nitinol or other memory metal materials.

Referring FIGS. 8 and 9, when the needle rod adjusting structure 13 is located at the rear end of the needle rod adjusting groove 1101, the effective needle rod segment 4 reaches the minimum length, and the spring-like second gas inlet tube 702 can be in a natural state. The needle rod lever is shifted and adjusted forward, the needle rod lever will drive the entire needle rod adjusting structure 13 and the needle rod 3 to move forward in the axial direction, so that the effective needle rod segment 4 becomes longer and the spring-like second gas inlet tube 702 is gradually stretched.

Referring to FIG. 10, when the needle rod adjusting structure 13 moves to the front end of the needle rod adjusting groove 1101, the effective needle rod segment 4 reaches the maximum length, and in this case the spring-like second gas inlet tube 702 is in the maximum stretched state.

Referring to FIG. 8, when the needle rod adjusting structure 13 is located at the rear end of the needle rod adjusting groove 1101 and the targeting region adjusting structure 10 is located at the rear end of the targeting region adjusting groove 1303, the effective needle rod segment 4 reaches the minimum length, and in this case the spring-like second gas inlet tube 702 is in a natural state without being stretched. In the specific implementation process, the spring-like second gas inlet tube 702 may be located in the front-segment heat-insulated tube 1 at this time, which may help reduce the length of the handle 11.

Referring to FIG. 9, when the position of the needle rod adjusting structure 13 is unchanged and the targeting region adjusting structure 10 is adjusted forward, the length of the needle rod 3 does not change but the length of the targeting region 5 is reduced, and the stretching and contraction state of the spring-like second gas inlet tube 702 remains unchanged; however, since the front-segment heat-insulated tube 1 moves forward, the second gas inlet tube 702 can come out of the front-segment heat-insulated tube 1. When the targeting region adjusting structure 10 is adjusted to the front end of the targeting region adjusting groove 1303, the length of the effective needle rod segment is still in the minimum state and the targeting region reaches the minimum length.

Referring to FIG. 10, when the needle rod adjusting structure 13 is adjusted forward and the position of the targeting region adjusting structure 10 relative to the targeting region adjusting groove 1303 remains unchanged, the length of the effective needle rod segment will gradually increase but the length of the targeting region remains unchanged, and the spring-like second gas inlet tube 702 is gradually stretched. When the needle rod adjusting structure 13 is adjusted to the foremost end of the needle rod adjusting groove, the length of the targeting region is still minimum, but the length of the needle rod reaches the maximum, and the gas inlet tube 702 is in the maximum stretched state.

In addition, the handle 11 can prevent the needle rod 3 from being ejected by a high-pressure gas. However, if the material of the handle is plastic with a limited strength and can be aged easily and when the handle is broken, the needle rod 3 will no longer have any additional safety protection measures and be ejected by the high-pressure gas. Therefore, in the optional solution of this embodiment, the first gas inlet tube and the needle tip 301 can be fixedly connected, which adds another safety guarantee to prevent the needle rod 3 from being ejected by the high-pressure gas.

In an implementation, referring to FIG. 12, it can be understood as a further improvement on the basis of the implementation shown in FIG. 11, wherein the gas inlet structure 7 further comprises a finned tube 704 and a mandrel 705, the finned tube 704 is wound around the mandrel 705, the front end of the finned tube 704 is connected to the rear end of the second gas inlet tube 702, and the rear end of the finned tube 704 is directly or indirectly connected to the gas inlet passage 703. The position of the mandrel 705 may be fixed relative to the rear-segment heat-insulated tube 2 and the handle 11.

In the specific implementation process, the mandrel 705, the gas inlet passage 703 and the gas return passage 8 can be welded and fixed to the rear end of the rear-segment heat-insulated tube 2. The first gas inlet tube 701, the second gas inlet tube 702, the finned tube 704, and the gas inlet passage 703 can be welded and fixed in sequence.

In addition, the finned tube can also be replaced by a spring-like second gas inlet tube. When the finned tube is replaced with the second gas inlet tube, a mandrel may be inserted in the spring-like second gas inlet tube, or heat exchanging fins may also be added to the outer surface of the spring.

That is, in an example, the gas inlet structure 7 further comprises a mandrel, the second gas inlet tube is wound around the mandrel, and the position of the mandrel is fixed relative to the rear-segment heat-insulated tube. The heat exchanging fins are arranged on the surface of the second gas inlet tube.

It can be seen that no matter whether the finned tube 704 and the mandrel 705 are provided, it does not depart from the description of this embodiment. Moreover, the solution without the finned tube 704 is beneficial to reducing the length of the entire handle 11, and the solution with the finned tube 704 and the mandrel 705 is beneficial to improving the position stability of the gas inlet structure 7.

The mandrel 705 mentioned above may be a hollow tubular structure. The hollow space can be used, for example, for a temperature measurement wire to pass through. The temperature measurement wire can be extended to the foremost end of the heat-insulated tube to measure the temperature at this position and make a feedback to the back end. The space between temperature measurement wire and the mandrel can be filled with glue and sealed.

In the specific implementation process, the first gas inlet tube 701 is also provided with a throttle hole 706. In an example, the throttle hole 706 may always be located on a side at the front end of the heat-insulated tube, so as to ensure that under any adjustment position, the throttle hole 706 is always located inside the targeting region.

Referring to FIG. 5 and in conjunction with other drawings, the adjustable cryoablation needle further comprises a needle rod sealing assembly 12 located at the rear end of the needle rod 3, and the needle rod sealing assembly 12 can be fixedly arranged at the rear end of the needle rod 3 and is used to seal a gap between the inner wall of the needle rod 3 and the outer wall of the front-segment heat-insulated tube 1. The needle rod sealing assembly 12 can effectively prevent the gas inside the needle from leaking out.

In the specific implementation process, the needle rod sealing assembly 12 may comprise a needle rod front retainer gasket 1202, a needle rod sealing gasket 1201, and a needle rod rear retainer gasket 1203.

The needle rod front retainer gasket 1202 can be connected to the outer side of the needle rod 3 and extend backwards to a side of the rear end of the needle rod 3. The needle rod rear retainer gasket 1203 can be connected to the inner side of the needle rod front retainer gasket 1202 and is located on a side at the rear end of the needle rod 3, and further, the inner side of the needle rod front retainer gasket 1202, a side at the rear end of the needle rod 3 and a side at the front end of the needle rod rear retainer gasket 1203 may form an accommodating space for accommodating the needle rod sealing gasket 1201.

Wherein, the needle rod front retainer gasket 1202 and the needle rod rear retainer gasket 1203 can be connected together by a thread structure.

Referring to FIG. 3, FIG. 11 and FIG. 12 and in conjunction with other drawings, the adjustable cryoablation needle further comprises a rear heat-insulated tube sealing assembly 9 located at the front end of the rear-segment heat-insulated tube 2, the rear heat-insulated tube sealing assembly 9 can be fixedly arranged at the front end of the rear-segment heat-insulated tube 2; this embodiment does not exclude implementations in which the rear heat-insulated tube sealing assembly 9 is arranged on the handle 11 or other embodiments of structures. The rear heat-insulated tube sealing assembly 9 is used to seal the gap at the inner side of the inner wall of the rear-segment heat-insulated tube 2.

In an example, if the needle rod 3 is inserted into the front end of the rear-segment heat-insulated tube 2, then the rear heat-insulated tube sealing assembly 9 is used to seal the gap between the outer wall of the needle rod 3 and the inner wall of the rear-segment heat-insulated tube 2.

In another example, if the front-segment heat-insulated tube 1 is inserted into the rear-segment heat-insulated tube 2 and the needle rod is not inserted into the rear-segment heat-insulated tube, then the rear heat-insulated tube sealing assembly 9 is used to seal the gap between the outer wall of the front-segment heat-insulated tube 1 and the inner wall of the rear-segment heat-insulated tube 2.

The rear heat-insulated tube sealing assembly 9 can help prevent the cold gas inside the needle from leaking out.

In the specific implementation process, the rear heat-insulated tube sealing assembly 9 may comprise a rear heat-insulating front retainer gasket 902, a rear heat-insulated tube sealing gasket 901, and a rear heat-insulated tube rear retainer gasket 903.

The rear heat-insulated tube rear retainer gasket 903 can be connected to the front end of the rear-segment heat-insulated tube 2, and the rear heat-insulated tube front retainer gasket 902 can be connected to the rear heat-insulated tube rear retainer gasket 903 from the inner side and front side of the rear heat-insulated tube rear retainer gasket 903; wherein a side at the rear end of the rear heat-insulated tube front retainer gasket 902, a side at the front end of the rear heat-insulated tube rear retainer gasket 903, and the inner side of the rear heat-insulated tube rear retainer gasket may form a space for accommodating the rear heat-insulated tube sealing gasket 901.

Wherein, the rear heat-insulated tube front retainer gasket 902 and the rear heat-insulated tube rear retainer gasket 903 can be connected together by a thread structure.

In the specific implementation process, the rear heat-insulated tube rear retainer gasket 903 can seal the gap connected to the rear-segment heat-insulated tube 2.

In an implementation, referring to FIG. 7 and in conjunction with other drawings, the front-segment heat-insulated tube 1 comprises a front-segment inner tube 102 and a front-segment outer tube 101; a front-segment vacuum interlayer is formed between the front-segment inner tube 102 and the front-segment outer tube 101; the front end of the front-segment inner tube 102 is connected with the front end of the front-segment outer tube 101, and the rear end of the front-segment inner tube 102 is connected with the rear end of the front-segment outer tube 101. In the specific implementation process, at least one end of the front-segment vacuum interlayer can be vacuum welded and sealed, thus forming a permanent vacuum interlayer.

In the specific implementation process, referring to FIG. 7, the rear end of the front-segment inner tube 102 and the rear end of the front-segment outer tube 101 can be connected by a heat-insulated tube gasket 103, and the rear end of the heat-insulated tube gasket 103 has a tapered inner hole. Further, the tapered inner hole can be used for external connection.

The heat-insulated tube gasket 103 can be used as a gap liner between the front-segment outer tube 101 and the front-segment inner tube 102.

In an implementation, referring to FIG. 3, the inner diameter and outer diameter of the front-segment heat-insulated tube 1 main remain unchanged. In another implementation, referring to FIG. 7, the front-segment heat-insulated tube 1 comprises a first tube segment 104, a connecting tube segment 106, and a second tube segment 105 in the axial direction, respectively; the rear end of the first tube segment 104 is connected to the front end of the connecting tube segment 106, the rear end of the connecting tube segment 106 is connected to the front end of the second tube segment 105, the inner diameter of the second tube segment 105 is greater than the inner diameter of the first tube segment 104, and the outer diameter of the second tube segment 105 is greater than the outer diameter of the first tube segment 104.

The change of the inner diameter and the outer diameter is beneficial to achieve the limitation on the movement position of the front-segment heat-insulated tube 1 when the front-segment heat-insulated tube 1 moves relative to the needle rod 3. Moreover, by changing the inner diameter and the outer diameter, the first tube segment 104 of the front-segment heat-insulated tube 1 can be easily matched and inserted into the needle rod 3, and the second tube segment 105 of the front-segment heat-insulated tube 1 can be easily matched and inserted into the rear-segment heat-insulated tube 2.

In an implementation, referring to FIG. 11 and FIG. 12, the rear-segment heat-insulated tube 2 comprises a rear-segment inner tube 202 and a rear-segment outer tube 201, a rear-segment vacuum interlayer is formed between the rear-segment inner tube 202 and the rear-segment outer tube 201, the front end of the rear-segment inner tube 202 is connected with the front end of the rear-segment outer tube 201, and the rear end of the rear-segment inner tube 202 is connected with the rear end of the rear-segment outer tube 201.

Wherein the front end of the rear-segment inner tube 202 and the front end of the rear-segment outer tube 201 can be connected by the rear heat-insulated tube sealing assembly 9, and the rear end of the rear-segment inner tube 202 and the rear end of the rear-segment outer tube 201 can be vacuum welded and sealed, thus forming a permanent vacuum gap layer.

To sum up, in the adjustable cryoablation needle provided by this embodiment, the first axial distance between the front end of the rear-segment heat-insulated tube and the front end of the needle rod is adjustable, and the length of the effective needle rod segment of the adjustable cryoablation needle changes with the first axial distance, so the length of the effective needle rod segment in the adjustable cryoablation needle that can be used for needle insertion is changeable; and thus the present disclosure can freely change the length according to different treatment requirements, thereby satisfying various treatment requirements. Therefore, this embodiment can avoid the inconvenience caused by the fact that a doctor has to select the type of cryoablation needles, and can be well adapted to different needle insertion depths, so that the exposed needle rod part can be as short as possible, and the bending of the needle rod and an injury to human tissues such as tissue tearing can be avoided.

Moreover, the length of the targeting region (or effective freezing area) of the cryoablation needle is related to the freezing range. For example, if the targeting region becomes longer, an ice ball formed by freezing will be larger. In some technologies, since the length of the targeting region of the cryoablation needle is usually fixed, doctors have to choose cryoablation needles with different targeting region lengths according to the tumor size. It can be seen that even if the length of the effective needle rod segment is indeed changeable, if the length of the targeting region remains the same, it is difficult to meet the treatment requirements of tumors of different sizes with one cryoablation needle. Doctors still need to choose cryoablation needles with different targeting region lengths according to the tumor size.

Furthermore, in this embodiment, the length of the targeting region may also change as the length of the effective needle rod segment changes; thus, the length of the targeting region is controllable and no longer changes synchronously with the change of the effective needle rod segment; the length of the targeting region is not fixed either, and its change may have a certain degree of freedom and is not completely limited to the movement of the needle rod. Therefore, the present disclosure can use a cryoablation needle to meet different needle depths and at the same time to further meet the treatment requirements of tumors of different sizes, and there is no need to select different cryoablation needles for different tumor sizes.

In addition, in the optional solution, adjustment is achieved, and the position of the needle rod can be fixed relative to the J-T groove. By fixing the position of the needle rod relative to the J-T groove, the distance between the front end of the J-T groove and the needle tip will not be too large. Therefore, it can prevent the problem that an ice ball cannot completely cover the needle tip, thus preventing the risk of puncturing the organs and blood vessels. Moreover, it can also prevent the needle rod from being ejected by a high-pressure gas, further improving the safety.

Furthermore, it should be noted that the above examples are merely intended to describe technical solutions of the present disclosure rather than to limit them; although the present disclosure has been described in detail with reference to the foregoing examples, those of ordinary skill in the art should understand that: it is still possible to modify the technical solutions described in the foregoing examples, or equivalently substitute some or all of technical features; and these modifications or substitutions do not make the nature of the corresponding technical solutions depart from the scope of the technical solutions of the examples of the present disclosure.

What is claimed is:

1. An adjustable cryoablation needle, comprising a needle rod, a front-segment heat-insulated tube and a gas inlet structure penetrating the needle rod and the front-segment heat-insulated tube, wherein the front-segment heat-insulated tube is inserted into the needle rod from a rear end of the needle rod, the front-segment heat-insulated tube can move relative to the needle rod in the axial direction of the needle rod, the gas inlet structure comprises a first gas inlet tube and a spring-like second gas inlet tube, a front end of the first gas inlet tube extends to the needle rod, and a rear end of the first gas inlet tube is connected to the front end of the second gas inlet tube, wherein the adjustable cryoablation needle further comprises a rear-segment heat-insulated tube, and the front-segment heat-insulated tube is connected to the rear-segment heat-insulated tube from a front end of the rear-segment heat-insulated tube;

the needle rod is configured to move relative to the rear-segment heat-insulated tube in the axial direction of the rear-segment heat-insulated tube, so as to adjust a first axial distance between the front end of the rear-segment heat-insulated tube and the front end of the needle rod;

the front-segment heat-insulated tube is configured to move relative to the rear-segment heat-insulated tube in the axial direction of the rear-segment heat-insulated tube, so as to adjust a second axial distance between the front end of the front-segment heat-insulated tube and the front end of the rear-segment heat-insulated tube;

wherein the length of an effective needle rod segment of the adjustable cryoablation needle changes with the first axial distance;

when the length of the effective needle rod segment changes, the front-segment heat-insulated tube is configured to move relative to the needle rod in the axial direction of the needle rod, so that the length of a targeting region of the adjustable cryoablation needle changes with the difference between the first axial distance and the second axial distance, the position of the first gas inlet tube is fixed relative to the needle rod, the rear end of the second gas inlet tube is directly or indirectly connected to a gas inlet passage, the position of the gas inlet passage is fixed relative to the rear-segment heat-insulated tube, and the second gas inlet tube is configured to be compressed or stretched in the axial direction.

2. The adjustable cryoablation needle according to claim 1, further comprising a needle rod adjusting structure configured to drive the needle rod to move relative to the rear-segment heat-insulated tube in the axial direction of the rear-segment heat-insulated tube, wherein the needle rod adjusting structure is fixedly connected to the outer side of the needle rod.

3. The adjustable cryoablation needle according to claim 2, further comprising a handle;

wherein the needle rod is inserted into the handle from the front end of the handle, and the rear-segment heat-insulated tube is configured in the handle and is fixed relative to the handle; the length of the effective needle rod segment is an axial distance between the front end of the handle and the front end of the needle rod; a tube wall of the handle is provided with a needle rod adjusting groove in the axial direction, and the needle rod adjusting structure passes through the needle rod adjusting groove and is configured to move along the needle rod adjusting groove.

4. The adjustable cryoablation needle according to claim 3, further comprising a targeting region adjusting structure configured to drive the front-segment heat-insulated tube to move relative to the rear-segment heat-insulated tube in the axial direction, wherein the targeting region adjusting structure is fixedly connected to the outer side of the front-segment heat-insulated tube.

5. The adjustable cryoablation needle according to claim 4, wherein the needle rod adjusting structure is provided with a targeting region adjusting groove in the axial direction, and the targeting region adjusting structure passes through the targeting region adjusting groove and is configured to move along the targeting region adjusting groove.

6. The adjustable cryoablation needle according to claim 5, wherein the targeting region adjusting structure comprises a targeting region slider fixedly connected to the front-segment heat-insulated tube and a targeting region lever connected to the targeting region slider, and the targeting region lever is extended to outside the needle rod adjusting groove and/or the targeting region adjusting groove.

7. The adjustable cryoablation needle according to claim 5, wherein the needle rod adjusting structure comprises a needle rod slider fixedly connected to the needle rod and a needle rod lever connected to the needle rod slider, and the needle rod lever is located outside the needle rod adjusting groove.

8. The adjustable cryoablation needle according to claim 7, wherein the targeting region adjusting groove is formed in the needle rod lever.

9. The adjustable cryoablation needle according to claim 1, wherein the gas inlet structure further comprises a finned tube and a mandrel, the finned tube is wound around the mandrel, the front end of the finned tube is connected to the rear end of the second gas inlet tube, the rear end of the finned tube is directly or indirectly connected to the gas inlet passage, and the position of the mandrel is fixed relative to the rear-segment heat-insulated tube.

10. The adjustable cryoablation needle according to claim 1, wherein, when the effective needle rod segment reaches the minimum length, the second gas inlet tube is in a natural state without being stretched.

11. The adjustable cryoablation needle according to claim 1, wherein the material of the second gas inlet tube is any one of the following: stainless steel, spring steel and memory metal material.

12. The adjustable cryoablation needle according to claim 1, wherein the gas inlet structure further comprises a mandrel, the second gas inlet tube is wound around the mandrel, and the position of the mandrel is fixed relative to the rear-segment heat-insulated tube.

13. The adjustable cryoablation needle according to claim 12, wherein heat exchanging fins are arranged on the surface of the second gas inlet tube.

14. The adjustable cryoablation needle according to claim 1, further comprising a needle rod sealing assembly located at the rear end of the needle rod, wherein the needle rod sealing assembly is configured to seal a gap between the inner wall of the needle rod and the outer wall of the front-segment heat-insulated tube.

15. The adjustable cryoablation needle according to claim 1, further comprising a rear heat-insulated tube sealing assembly located at the front end of the rear-segment heat-insulated tube, wherein the rear heat-insulated tube sealing assembly is configured to seal a gap at the inner side of the inner wall of the rear-segment heat-insulated tube.

16. The adjustable cryoablation needle according to claim 1, wherein the front-segment heat-insulated tube comprises a front-segment inner tube and a front-segment outer tube, a front-segment vacuum interlayer is formed between the front-segment inner tube and the front-segment outer tube, the front end of the front-segment inner tube is connected to the front end of the front-segment outer tube, and the rear end of the front-segment inner tube is connected with the rear end of the front-segment outer tube.

17. The adjustable cryoablation needle according to claim 16, wherein the rear end of the front-segment inner tube and the rear end of the front-segment outer tube are connected by a heat-insulated tube gasket, and the rear end of the heat-insulated tube gasket has a tapered inner hole.

18. The adjustable cryoablation needle according to claim 17, wherein the front-segment heat-insulated tube has a first tube segment, a connecting tube segment, and a second tube segment in the axial direction, respectively; the rear end of the first tube segment is connected to the front end of the connecting tube segment, the rear end of the connecting tube segment is connected to the front end of the second tube segment, the inner diameter of the second tube segment is greater than the inner diameter of the first tube segment, and the outer diameter of the second tube segment is greater than the outer diameter of the first tube segment.

19. The adjustable cryoablation needle according to claim 1, wherein the rear-segment heat-insulated tube comprises a rear-segment inner tube and a rear-segment outer tube, a rear-segment vacuum interlayer is formed between the rear-segment inner tube and the rear-segment outer tube, the front end of the rear-segment inner tube is connected with the front end of the rear-segment outer tube, and the rear end of the rear-segment inner tube is connected with the rear end of the rear-segment outer tube.

20. The adjustable cryoablation needle according to claim 2, wherein the gas inlet structure further comprises a finned tube and a mandrel, the finned tube is wound around the mandrel, the front end of the finned tube is connected to the rear end of the second gas inlet tube, the rear end of the finned tube is directly or indirectly connected to the gas inlet passage, and the position of the mandrel is fixed relative to the rear-segment heat-insulated tube.

* * * * *